Figure 1:
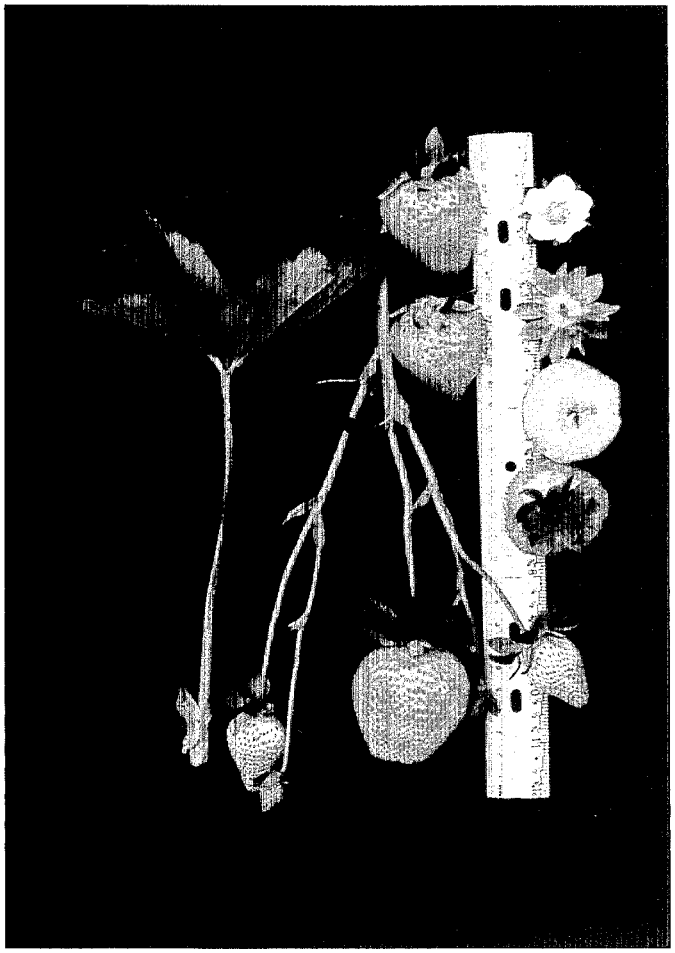

US00PP08745P

United States Patent [19]

Sjulin et al.

[11] Patent Number: Plant 8,745

[45] Date of Patent: May 24, 1994

[54] STRAWBERRY PLANT CALLED 'AVILA'

[75] Inventors: Thomas M. Sjulin, Watsonville; Amado Q. Amorao, Camarillo; Joseph I. Espejo, Jr., Watsonville, all of Calif.

[73] Assignee: Driscoll Strawberry Associates, Inc., Watsonville, Calif.

[21] Appl. No.: 37,063

[22] Filed: Mar. 25, 1993

[51] Int. Cl.[5] ..... A01H 5/00

[52] U.S. Cl. ..... Plt./48

[58] Field of Search ..... Plt. 48, 49

*Primary Examiner*—James R. Feyrer

*Attorney, Agent, or Firm*—Townsend and Townsend Khourie and Crew

[57] ABSTRACT

'V258' is a spring bearing variety of strawberry plant characterized by its ability to produce a strong plant, which remains in production consistently from April to October in the central coastal area of California if given adequate chilling before and after being winter planted.

The variety is particularly distinguished by its large, light colored, multi-crowned plant, its large crown and main crop berries, with light colored surface and firm flesh and by its consistently high quality strawberry flavor.

1 Drawing Sheet

DESCRIPTION

This invention relates to a new and distinct short day winter-planted spring bearing variety of strawberry plant identified and designated as 'Avila' which is a result of a cross of 'Chandler', U.S. Plant Pat. No. 5,262, and Driscoll Strawberry Associates, Inc. variety 'Commander', U.S. Plant Pat. No. 7,024. The variety is botanically identified as *F.* ×*ananassa* Duch.

The seedlings resulting from the aforementioned cross were grown and asexually multiplied by stolon runners in Shasta County in a propagating nursery and other runner plants of each seedling clone were taken for testing to fruiting beds on the property of Driscoll Strawberry Associates, Inc. The runners from clones of the seeding held in the Shasta County propagating nursery were set for further nursery propagation and for further testing at the fruiting beds. One plant was selected from the aforementioned group of seedlings and further asexually reproduced in the Shasta County nursery of Driscoll Strawberry Associates, Inc. Tests followed in various parts of California and Florida during intervening seasons on various properties of grower members of the Driscoll Strawberry Associates, Inc. These tests indicated the merits of 'V258' and resulted in its selection as a promising commercial variety. Subsequent tests on Driscoll strawberry grower-controlled land proved that the variety had commercial value in California, but not in Florida.

In the drawing, FIG. 1 shows plant parts of the new variety, typical in size, shape and color.

The berry, in cross section, illustrates flesh color and characteristic core cavity. The inflorescence illustrates typical branching and relative size about the middle of May. The inflorescence total length is long, as are the pedicel and the common peduncle. The diameter of the pedicel holding the primary berry is not small but is not as large as other Driscoll Strawberry Associates varieties such as 'Swede', U.S. Plant Pat. No. 6,191. The pedicel housing the primary berry shown in the drawing originates from a secondary peduncle not the axil of secondary peduncles which is often the case. The drawing illustrates typical fruit shape of both the ripe and green fruit present during May. There is some ribbing on the primary berry with green tips and a noticeable lack of seed under the calyx. This skin under the calyx is prone to crack as is pictured on the berry that is cut in half and has its calyx facing the camera. The calyx shown is only slightly reflexed which is common, and may be more reflexed later in the season giving the berry a necked appearance. The sepals shown in the drawing are mostly without serrations, but serrations can be present as shown in the sepals of the primary berry that is pictured. The leaf shown is typical with leaflets cupped upward with a long petiole without a bract present, but bracts may be present at times. The leaflet serrations are large, but not sharp at the apex. The central leaflet has small extra serrations at the union of two serrations and this is typical of many leaflets, and is a distinctive character of the new variety.

The novel plant of 'Avila' is large in size becoming dense in the fall if given adequate chilling before being planted and given adequate nitrogen fertilizer. This plant is larger with more crowns and runners per plant than the 'Swede' variety. It is also lighter in color than 'Swede', especially in the summer and fall. As the fruiting season develops, the difference in plant size becomes greater. Table 1 illustrates the difference in width and height of the 'Avila' plant as compared to 'Swede' and 'Commander'. The winter-planted 'Avila' is capable of producing fruit of good size and quality during the entire fruiting seaons. While 'Avila' is not an everbearer, it is capable of long season fruit production when grown in the central coast area of California. When dug at a high elevation nursery in northern California when the plants receive a minimum chilling before being dug and are given adequate cold storage (33 degrees Fahrenheit) after being dug, long season production can be obtained. If excessive chilling is given before planting such as a planting date in February having been dug in November, no fruit production subsequent to the crown crop would be obtained the first year after being planted. If 'Avila' were an everbearer, production after the crown crop would be obtained even though planted in February. The production, if given prior chilling, occurs from late March to November if rain or cold temperatures do not prevent picking. If chilling exceeds these guidelines, some production may be obtained after the crown crop, but excessive runners and plant growth are obtained. Table 2 illustrates 'Avila' is actually earlier than 'Swede' and its total production is equal. Its average fruit size is slightly smaller. The crown crop fruit (fruit from flowers initiated while at the nursery) are large and not as prone to split at the apex as is the variety 'Swede'. 'Avila' also varies from 'Swede' in that its fruit tends to be long conic or wedge and not with the heavy shoulders and lack of necking of 'Swede'. Throughout the season, the fruit of 'Swede' is more exposed because of the open plant of 'Swede' and during the summer and fall, the fruit size is larger. The flesh firmness and skin strength of the new variety is superior to 'Swede'. Replicating holding tests ratings from May through September rated the skin strength of 'Avila' 7.40 and flesh firmness 7.55 as compared to 'Swede' skin 6.06 and flesh 5.63 (higher the number the stronger then skin and firmer the flesh). Seed of the new variety is held more inserted in relationship with the skin surface than 'Swede'. There are also less seeds per given surface area of the new variety, especially during late summer and fall on secondary and tertiary berries. As the fruit ripens, 'Swede' becomes darker sooner than does the 'Avila' and even after a period of holding out of cold storage, 'Avila' is noticeably ligher in color, especially during the summer and fall. 'Swede' also has a more noticeable gloss to its skin than the new variety. Flavor panels have rated this new variety equal to that of 'Swede', and the strawberry aroma is as noticeable as that of 'Swede'(See Table 3). During July, after more than a week in cold storage, 'Avila' fruit produced 7.9% soluble solids and 'Swede' produced 7.3% and 'Commander' 7.7%. In Watsonville, 'Avila' when planted by November 1, will produce its peak crown crop production during mid-April, which is similar to 'Swede', while in Florida, if planted in mid-October, it will produce its crown crop during mid-December. This crown crop production in Watsonville is earlier than that of 'Commander', Driscoll Variety U.S. Plant Pat. No. 7,024, one of the parents of 'Avila'. If both 'Commander' and 'V258' are planted at their ideal planting date, in central coastal California the 'Avila' plant will produce more runners per plant and will become denser in the fall than 'Commander'. When measured during July and August, Table 4 verifies the large plant of 'Avila' when comparing petiole length to 'Swede'. The fruit of 'Avila' ripens farther from the crown, and often in the ditch free of the plant canopy, as the total inflorescence length of the new variety is longer than that of 'Swede'. The common peduncle during August of 'Avila' averages 17 cm and 'Swede' averages 8 cm. The hair on pedicels remains irregularly parallel to the pedicel in contrast to 'Swede', whose hair is perpendicular to the pedicel.

Even though 'V258' is considered an early variety, it will not crop as early as 'Chandler', one of its parents, if each variety is planted at the same time. It does, however, have the ability to crop more consistently in the summer and fall and its fruit size is larger. It also is considered to have a better flavor than 'Chandler'. The crown crop fruit shape is considered smoother than 'Chandler'.

'V258' is susceptible to verticillium wilt, the anthracnose disease caused by *Colletotrichum acutatum*, but it has not been severely susceptible to powdery mildew, Mycosphaerella leaf spot, angular leaf spot or Botrytis. During rainy or wet periods, however, it will show injury. The plant is susceptible to injury from two-spotted spider mite as well as flower thrip. As a seedling and selection, it withstood without noticeable injury the natural infection of the known common virus components present in California.

The varietal characteristics of the novel plant described in detail were observed in May and June in Watsonville, Calif., which is near the Pacific Ocean. Some characters were rated at a different time and the date is listed with the rate. The measurements were made from plants planted in November and were dug at a high elevation nursery in October. Many characters, such as crop, fruit size and shape and plant size and color will vary during the summer and fall.

The color terminology is in accordance with the Munsell Color system.

Plant: Large with multiple crowns if given ample chilling before planting, becoming larger during summer and fall. This plant may produce a dense canopy in central coastal California. Table 1 illustrates length and width during July and August. The plant is considered light in color.

Leaves: Medium to large in size, central leaflet is usually 5 to 10 cm in width and length with large serrations at margins, but not noticeably pointed at the apex. See Table 3, (illustrates the size of these serrations as compared to 'Swede' and 'Commander'). Many leaflets have small double serrations at the point where the serrations join. Petiole length is considered long, 15 to 25 cm, when measuring from crown bracts to pediolule. Bracts may be present on petioles. Color of upper side of the leaflet is 8.1GY-3.7/7.6 to 8.2GY-3.2/6.1. Color of leaflet underside during July and August is 4.5GY-3.9/6.9. The petiole color in August in 5.4GY-6.9/12.6.

Isozymes in leaf extract: phosphoglucoisomerase (PGI) 3-banded A1. Leucine aminopephgase (LAP) 2-banded B3, Phosphoglucomutase (PGM) 2-banded C4. (1). This testing was done by Driscoll Strawberry Associates Laboratory following the procedure described in publication: Electrophoretic Characterization of California Strawberry Cultivars by Bringhurst, 1981. See Table 5.

Runners: Runners are vigorous and considered abundant at the nursery and in the fruiting beds, especially if given more than ideal chilling before or after being transplanted.

Inflorescence: Long in length, mostly 35 to 40 cm with the common peduncle also long, mostly 10 to 20 cm in length. Pedicel holding primary berries, medium to thick in diameter, to 2 to 3 mm and considered long. Pedicel holding primary berries may originate from an axil of secondary peduncles or on one of the peduncles. Hair on pedicel is irregularly parallel to the pedicel. Some flowers are usually visible above the plant. Anthers produce an abundance of pollen even during the early spring. The average member of petals of primary flowers during August is 6.1 with the width of individual petals 13.7 mm and the length 12.5 mm as compared to 'Swede' at the same time with 6.6 petals and the width is 13.1 and the length is 11.9 mm. The diameter of pistils of these same flowers averages 5.9 mm for 'Avila' and 7.9 mm for 'Swede'.

Fruit: The crown crop size is large and attractive, usually equal to or larger than those produced by the main crop. Primaries of the main crop are 40 to 50 mm in length and width with the length generally slightly greater than the width. Primaries are mostly medium conic to medium wedge in outline with the secondary and tertiaries mostly symmetrically conic as illustrated in the U.S.D.A. Bulletin No 1043. The fruit surface is smooth, except some primaries may have slight longitudinal furrows present and, as the fruiting season progresses, the seeds are held in inserted positions in relationship to the fruit surface giving some berries a sunken appearance. The shape also becomes irregular during summer and fall, often becoming necked in appearance with the lack of seed under the calyx. This area under the calyx may crack but heals and doesn't seem to be a detriment to the fruit quality. The flesh is considered noticeably firm. The surface color is mostly 6.8R-3.7/15.8 to 6.6R-3.2/12.6 and darkens only slightly after being picked. The flesh color varies from 6.9R-4.9/16.6 to 5.8R4.3/16.6 to white at the core. The seeds are abundant, but as the season progresses, the space between seeds increases. The seeds are yellow but darken when exposed to direct sunlight.

Calyx: The calyx of primary berries is large, 40 to 50 cm. in diameter with overlapping sepals. The calyx is usually held free of the fruit and often reflexed. Sepals have some serrations present and are elliptical to ovate in outline with an acute apex. Color of the sepals facing fruit is 8.1GY-3.7/7.6 to 0.7G-3.4/8.5.

TABLE #1

AVERAGE PLANT SIZE -
Watsonville, California as of 8-2-93
Width - Leaf tip to leaf tip - centimeters
Height - Soil to top leaf - centimeters
(Plants grown over 8" plastic covering drip irrigation.)

| AVILA | | KEY LARGO | | SWEDE | | COMMANDER | |
|---|---|---|---|---|---|---|---|
| W | H | W | H | W | H | W | H |
| 45.8 | 33.6 | 40.0 | 24.5 | 37.7 | 24.5 | 44.1 | 27.7 |

TABLE #2

1992 marketable fruit yield and size comparison of Nursery-grown high elevation (McArthur, California) Avila compared to Swede dug October 7, 1991 and planted November 6, 1991 in Watsonville, California.

MONTHLY YIELD IN GRAMS PER PLANT

| VARIETY | APR | MAY | JUN | JUL | AUG |
|---|---|---|---|---|---|
| AVILA | 97 | 278 | 287 | 151 | 299 |
| SWEDE | 85 | 194 | 269 | 318 | 235 |

| VARIETY | SEP | OCT | TOTAL G/PL | SIZE G/FR |
|---|---|---|---|---|
| AVILA | 302 | 148 | 1560 | 25.7 |
| SWEDE | 246 | 160 | 1508 | 26.2 |

TABLE 3

1992 FLY RANCH TIME OF PLANTING
FLAVOR TEST SUMMARY

| EVAL DATE | RATE DATE | AVERAGE FLAVOR SCORE AVILA | KEY LARGO | COM-MANDER | SWEDE |
|---|---|---|---|---|---|
| 05/26/92 | 06/03/92 | 3.8 | 3.9 | 3.6 | 3.8 |
| 06/02/92 | 06/09/92 | 3.9 a | 3.3 bc | 3.1 c | 3.7 ab |
| 06/16/92 | 06/24/92 | 3.8 a | 3.5 a | 2.9 b | 3.7 a |
| 06/30/92 | 07/01/92 | 3.5 a | 3.9 a | 2.6 b | 3.5 a |
| 06/24/92 | 07/02/92 | 3.8 | 3.7 | 3.4 | 3.4 |
| 07/07/92 | 07/15/92 | | 3.1 | 3.5 | 3.3 |
| 07/14/92 | 07/22/92 | | 3.0 b | 2.3 c | 3.0 ab |
| 07/28/92 | 08/05/92 | 3.0 a | 3.4 a | 2.9 a | 2.8 a |
| 08/04/92 | 08/12/92 | | | 3.1 | 3.1 |
| 08/11/92 | 08/18/92 | | | 3.1 | 3.5 |
| 08/18/92 | 08/27/92 | | 3.7 a | 2.9 bc | 3.0 abc |
| 08/25/92 | 09/02/92 | | 3.0 | 3.3 | 2.8 |
| 09/01/92 | 09/09/92 | | 3.7 a | 3.0 bc | 3.5 ab |
| 09/15/92 | 09/22/92 | | 3.4 a | 2.9 b | 3.5 a |
| 09/29/92 | 10/07/92 | | 3.5 ab | 2.8 c | 4.0 a |
| AVERAGE: | | 3.6 | 3.5 | 3.0 | 3.4 |

**Significantly different at or below the 1% level.

TABLE 3-continued

1992 FLY RANCH TIME OF PLANTING
FLAVOR TEST SUMMARY

| DATE | DATE | # OF EVAL. | LEVEL OF SIGN. |
|---|---|---|---|
| 05/26/92 | 06/03/92 | 17 | 0.843 |
| 06/02/92 | 06/09/92 | 15 | 0.002** |
| 06/16/92 | 06/24/92 | 12 | 0.002** |
| 06/30/92 | 07/01/92 | 16 | 0.000** |
| 06/24/92 | 07/02/92 | 12 | 0.072 |
| 07/07/92 | 07/15/92 | 12 | 0.494 |
| 07/14/92 | 07/22/92 | 11 | 0.000** |
| 07/28/92 | 08/05/92 | 13 | 0.002** |
| 08/04/92 | 08/12/92 | 11 | 0.061 |
| 08/11/92 | 08/18/92 | 7 | 0.234 |
| 08/18/92 | 08/27/92 | 10 | 0.000** |
| 08/25/92 | 09/02/92 | 6 | 0.194 |
| 09/01/92 | 09/09/92 | 14 | 0.000** |
| 09/15/92 | 09/22/92 | 15 | 0.001** |
| 09/29/92 | 10/07/92 | 11 | 0.002** |

TABLE #4

Leaf Characteristics of Avila, Swede and Commander - Watsonville, California, July 13, 1993.

| | SERRATION DEPTH mm* | PETIOLE LENGTH cm** |
|---|---|---|
| AVILA | 5.45 | 21.8 |
| SWEDE | 4.48 | 15.4 |
| COMMANDER | 4.21 | 21.0 |

* = Measuring from serration apex to a line between where serrations join.
** = Measuring from petiolule to lowest point of basal bract.

TABLE #5

Avila Isozyme banding patterns compared to Swede and Commander

| CULTIVAR | PG1 | LAP | PGM |
|---|---|---|---|
| AVILA | A1 | B3 | C4 |
| SWEDE | A1 | B3 | C2 |
| COMMANDER | A4 | B3 | C4 |

We claim:

1. We claim the new and distinct variety of strawberry plant described and illustrated and identified by the characteristics enumerated above.

* * * * *